(12) United States Patent
McChesney et al.

(10) Patent No.: US 6,653,501 B2
(45) Date of Patent: Nov. 25, 2003

(54) CHIRAL RESOLUTION METHOD FOR PRODUCING COMPOUNDS USEFUL IN THE SYNTHESIS OF TAXANES

(75) Inventors: James D. McChesney, Boulder, CO (US); Herbert R. Brinkman, Superior, CO (US); Siead Zegar, Orland Park, IL (US); David Baehr, Waukegan, IL (US)

(73) Assignee: NaPro BioTherapeutics, Inc., Boulder, CO (US)

( * ) Notice: Subject to any disclaimer, the term of this patent is extended or adjusted under 35 U.S.C. 154(b) by 0 days.

(21) Appl. No.: 09/894,811

(22) Filed: Jun. 27, 2001

(65) Prior Publication Data

US 2003/0045743 A1 Mar. 6, 2003

(51) Int. Cl.$^7$ ........................ C07C 271/00; C07B 57/00
(52) U.S. Cl. ........................................ 560/29; 562/401
(58) Field of Search ............................ 560/29; 562/401

(56) References Cited

U.S. PATENT DOCUMENTS

| | | |
|---|---|---|
| 4,924,011 A | 5/1990 | Denis et al. |
| 4,924,012 A | 5/1990 | Colin et al. |
| 5,567,614 A | 10/1996 | Patel et al. |
| 5,675,025 A | 10/1997 | Sisti et al. |
| 5,684,175 A | 11/1997 | Sisti et al. |
| 5,686,298 A | 11/1997 | Patel et al. |
| 5,688,977 A | 11/1997 | Sisti et al. |
| 5,750,737 A | 5/1998 | Sisti et al. |
| 5,770,745 A | 6/1998 | Swindell et al. |
| 5,773,629 A | 6/1998 | Yang et al. |
| 5,811,292 A | 9/1998 | Patel et al. |
| 5,817,867 A | 10/1998 | Li et al. |
| 5,939,566 A | 8/1999 | Swindell et al. |
| 5,948,919 A | 9/1999 | Sisti et al. |
| 5,973,170 A | 10/1999 | Sisti et al. |
| 6,020,174 A | 2/2000 | Chen et al. |
| 6,025,516 A | 2/2000 | Ramaswamy et al. |
| 6,048,990 A | 4/2000 | Liang et al. |
| 6,066,749 A | 5/2000 | Sisti et al. |
| 6,072,060 A | 6/2000 | Swindell et al. |
| 6,107,497 A | 8/2000 | Sisti et al. |
| 6,133,462 A | 10/2000 | Sisti et al. |
| 6,136,999 A | 10/2000 | Chander et al. |
| 6,143,902 A | 11/2000 | Zygmunt et al. |

OTHER PUBLICATIONS

Hyun et al, Liquid Chromatographic Resolution of 2–Hydroxycarboxylic Acids On a New Chiral Stationary OPhase Derived from (S)–Leucine, 2000, Journal of Chromatography A, 868, pp. 31–39.*

Pirkle et al, Use of a Simultaneous Face to Face and Face to Edge pi–pi Interactions to Facilitate Chiral Recognition, 1994, Tetrahedron Asymmetry, 5, pp. 777–780.*

Still et al, Rapid Chromatographic Technique for Preparative Separations With Moderate Resolution, Journal of Organic Chemistry, 1978, 43, pp. 2923–2925.*

Srivastava and McChesney, A Practical and Inexpensive Synthesis of the Taxol C–13 Side Chain; N–Benzoyl–(2R, 3S)–3–Phenylisoserine, Natural Product Letters, 1995, pp. 147–152, vol. 6, Harwood Acadamic Publishers GmbH.

Denis et al., An Improved Synthesis of the Taxol Side Chain and of RP 56976, J. Org. Chem., 1990, pp. 1957–1959, vol. 55.

Bonini and Righi, Enantio– and Stereo–selective Route to the Taxol Side Chain via Asymmetric Epoxidation of trans–Cinnamyl Alcohol and Subsequent Epoxide Ring Opening, J. Chem. Soc., Chem. Commun., 1994, pp. 2767–2768.

Honig et al., Chemo–Enzymatic Synthesis of All Isomeric 3–Phenylserines and –Isoserines, Tetrahedron Letters., 1990, pp. 3841–3850, vol. 46.

Bachelor et al., The Darzens Glycidic Ester Condensation, J. Org. Chem, Nov. 1969, pp. 3600–3604, vol. 34, No. 11.

Koskinen et al.., Enantioselective Synthesis of the Taxol and Taxotere Side Chains, J. Chem. Soc., Chem. Commun., 1994, pp. 21–22.

Deng et al., A Practical, Highly Enantioselective Synthesis of the Taxol Side Chain via Asymmetric Catalysis, J. Org. Chem., 1992, pp. 4320–4323, vol. 57, No. 15.

Gou et al., A Practical Chemoenzymatic Synthesis of the Taxol C–13 Side Chain N–Benzoyl–(2R, 3S)–3–phenylisoserine, J. Org. Chem., 1993, pp. 1287–1289, vol. 58, No. 5.

* cited by examiner

Primary Examiner—Johann Richter
Assistant Examiner—Paul A. Zucker
(74) Attorney, Agent, or Firm—Timothy J. Martin; Michael R. Henson; Rebecca A. Gegick

(57) ABSTRACT

A method is provided for processing a solution having optical isomers to obtain a (2R,3S) target isomer:

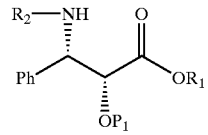

wherein $P_1$ is H or a hydroxyl protecting group, $R_1$ is H, an alkyl group, an olefinic group or an aromatic group, and $R_2$ is H or $R_3CO$, where $R_3$ is an alkyl group, an olefinic group, an aromatic group, an O-alkyl group, an O-olefinic group or an O-aromatic group, provided that $R^1$ is not H when $R^3$ is Ph and $P^1$ is H. The method includes passing the solution through a chromatographic stationary phase, such as S,S Whelk-O, that has a greater affinity for one of the target isomer and an optical isomer thereof. A portion of the solution with the target isomer is then collected. The solution may be a racemic mixture of (±)-N-CBZ-3-phenylisoserine ethyl ester.

39 Claims, 3 Drawing Sheets

CHIRAL RESOLUTION METHOD FOR PRODUCING COMPOUNDS USEFUL IN THE SYNTHESIS OF TAXANES

FIELD OF THE INVENTION

The present invention generally relates to the preparation of compounds useful in the semi-synthesis of taxanes. More particularly, the present invention is directed to the chiral resolution of mixtures of optical isomers to provide a target chiral compound that can be used as a C-13 side chain precursor to produce paclitaxel and other taxanes. The present invention specifically provides a chromatographic process for separating a target chiral compound from its enantiomer in a racemic mixture thereof.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel" which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity.

Paclitaxel is a naturally occurring taxane diterpenoid which is found in several species of the yew (genus Taxus, family Taxaceae). Unfortunately, the concentration of this compound in the yew is very low, and the species of evergreen are also slow growing. Even though the bark of the yew trees typically exhibits the highest concentration of paclitaxel, the production of one kilogram of paclitaxel requires approximately 16,000 pounds of bark. Thus, the long-term prospects for the availability of paclitaxel through isolation are discouraging.

While the presence of paclitaxel in the yew tree is in extremely low concentrations, there are a variety of other taxane compounds, such as baccatin III, cephalomanine, 10-deacetylbaccatin III, etc., which are also able to be extracted from the yew bark and leaves. Some of these other taxane compounds are more readily extracted in higher yields. Indeed, a relatively high concentration of 10-deacetylbaccatin III can be extracted from the leaves of the yew as a renewable resource.

Accordingly, attention has turned to the semi-synthesis of paclitaxel, which has the formula:

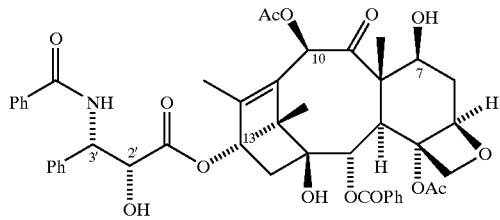

as well as other related taxanes, such as docetaxel, which has the formula:

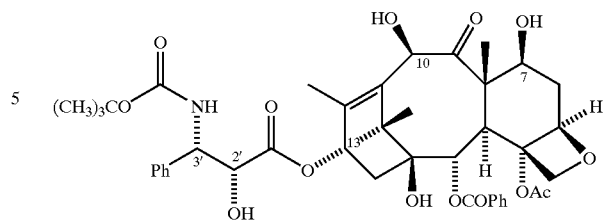

from precursor compounds. In order to successfully synthesize paclitaxel and other taxanes, convenient access to a chiral, non-racemic side chain acid is desired, as well as an abundant natural source of a usable baccatin III backbone. Various approaches have been developed for esterifying such a side chain acid at the 13-hydroxyl of baccatin III or 10-deacetyl baccatin III, or derivatives thereof, which respectively have the formulas:

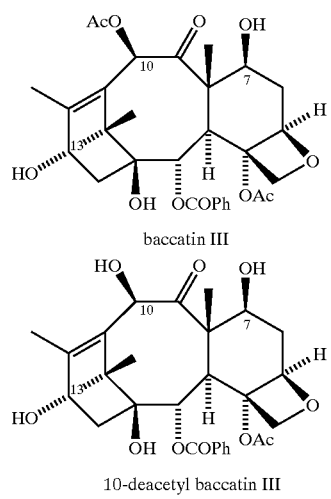

baccatin III 10-deacetyl baccatin III

The coupled ester product may then be converted to paclitaxel, docetaxel or other taxanes. For example, U.S. Pat. No. 4,924,011 to Denis et al. describes a process for preparing paclitaxel using a (2R,3S) side chain acid of the general formula:

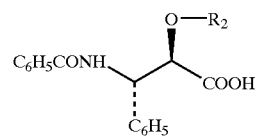

where $R_2$ is a hydroxy-protecting group. Additionally, U.S. Pat. No. 4,924,012 to Colin et al. describes a process for preparing taxanes, such as docetaxel, that uses an acid of formula:

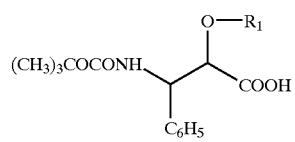

where $R_1$ is a hydroxy-protecting group. In the syntheses described by Denis et al. and Colin et al., the side chain acid is esterified with a baccatin III or 10-deacetyl baccatin III derivative, and the coupled product is thereafter deprotected, such as by replacing any protecting groups, including $R_2$ or $R_1$ in the above formulas, respectively, with hydrogen. It should be noted that the $C_6H_5CONH$— group of Denis et al. and the $(CH_3)_3COCONH$— group of Colin et al. are the final desired groups for the resulting paclitaxel and docetaxel products, respectively, such that no further chemical transformation at the nitrogen position is performed in the chemical syntheses disclosed therein.

U.S. Pat. No. 5,770,745 to Swindell et al. describes another early synthetic route in the semi-synthesis of paclitaxel, wherein the use of protecting groups to protect various positions of the taxane backbone and the side chain acid was investigated as a means of improving the chemical process to form paclitaxel, and of improving the esterification step in particular. Specifically, a side chain acid of the general formula:

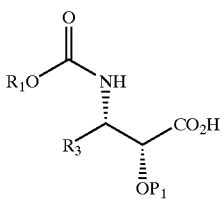

is described, wherein $R_1$ can be an alkyl, olefinic or aromatic group (such as $PhCH_2$), $R_3$ can be hydrogen or Ph, and $P_1$ can be a hydroxyl protecting group.

More recently, attention has been focused on the use of a 3-N-CBZ-2-O-protected (2R,3S)-3-phenylisoserine acid of the formula:

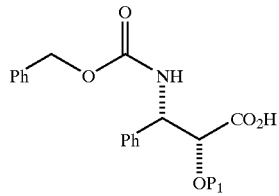

wherein $P_1$ is a hydrogenatable protecting group, such as benzyloxymethyl (BOM) or benzyl. Synthetic routes to produce taxanes such as paclitaxel or docetaxel using such a side chain are described, for example, in U.S. Pat. Nos. 5,675,025; 5,684,175; 5,688,977; 5,750,737; 5,939,566; 5,948,919; 5,973,170; 6,048,990; 6,066,749; 6,072,060; 6,107,497; 6,133,462; 6,136,999; and 6,143,902, and the teachings thereof are incorporated herein by reference.

As taught, for example, in U.S. Pat. No. 5,684,175 to Sisti et al., the 3-N-CBZ-2-O-protected (2R,3S)-3-phenylisoserine may be produced from a (2R,3S)-3-phenylisoserine ethyl ester starting compound of the formula:

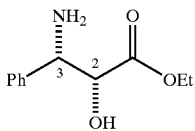

which may be protected at the 3'-N and 2'-O positions and saponified to the corresponding acid for use in the esterification step.

The formation of a 3-phenylisoserine alkyl ester is known in the art and is described, for example, in U.S. Pat. No. 4,924,012 to Colin et al. In particular, Colin et al. describes an epoxide of the formula:

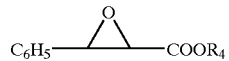

where $R_4$ denotes alkyl containing 1 to 4 carbon atoms, and preferably ethyl, which may be obtained under the conditions described by F. W. Bachelor and R. K. Bansal, J. Org. Chem., 34, 3600-04 (1969). This epoxide is converted to an azide of general formula:

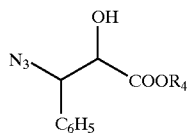

according to known methods for opening an epoxide by means of sodium azide in ethanol in the heated state. The azide is thereafter reduced to a 3-phenylisoserine alkyl ester of the formula:

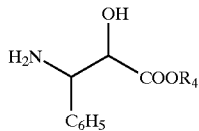

However, because this compound has two chiral centers (C-2 and C-3, respectively), processes to produce this compound may produce both the cis (2R,3S) and (2S,3R) enantiomers respectively, such as of the formulas:

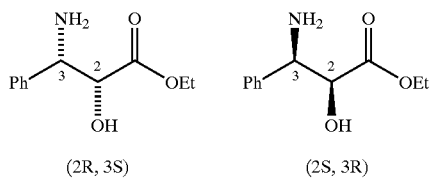

as well as their trans (2R,3R) and (2S,3S) diastereomers respectively of the formulas:

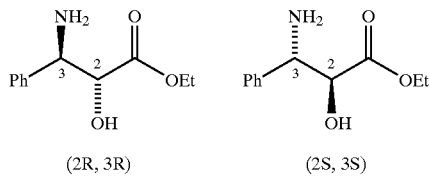

It should be appreciated that the above optical isomers are shown using an ethyl group for $R_4$ in the formulas above, although other alkyl esters as described in Colin et al. may be formed. Additionally, various other derivatives or analogs of these optical isomers may be formed in the processes to produce the paclitaxel side chain, in view of the teachings of the above-identified patents, as would be understood by the ordinarily skilled person.

While baccatin III and derivatives thereof may be used as a resolving agent to selectively recover products having the desired (2R,3S) configuration, such an approach is quite costly and results in a substantial yield reduction of the desired product. Accordingly, efficient and economical methods are needed for recovering a desired (2R,3S) isomer or a derivative thereof at one or more points in the chemical processes for synthesizing taxanes.

One procedure to prepare the chiral (2R,3S) C-13 side chain of paclitaxel is described by Srivastava and McChesney, "A Practical and Inexpensive Synthesis of the Taxol C-13 Side Chain; N-Benzoyl-(2R,3S)-3-Phenylisoserine", Natural Products Letters, Vol. 6, p. 147 (1995). This procedure involves the classical resolution of cis-3-phenylglycidic acid using D-(+)-ephedrine as the resolving agent. In particular, an optically pure cis-(2R,3R)-3-phenylglycidic acid-(+)-ephedrine salt of the formula:

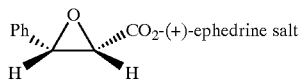

is recovered from a mixture of diastereomeric salts by fractional crystallization with acetone. The optically pure intermediate is then converted to a 3-phenylisoserine derivative. Additional classical resolutions of side chain derivatives useful in paclitaxel synthesis have been described in U.S. Pat. No. 6,025,516 to Ramaswamy et al. and in U.S. Pat. No. 5,817,867 to Li.

Several other procedures are reported in the literature to prepare chiral, cis-3-phenylglycidate derived intermediates useful in the partial synthesis of paclitaxel. Some examples include methodologies utilizing Sharpless asymmetric dihydroxylation (Denis et al., J. Org. Chem., 55, p.1957, 1990; Koskinen et al., J. Chem. Soc., Chem. Commun., p.21, 1994; and Bonini et al., J. Chem. Soc., Chem. Commun., p.2767, 1994) and some utilizing Jacobsen's asymmetric epoxidation (Deng et al., J. Org. Chem., 57, p.4323, 1992). Other references have reported chemoenzymatic resolution methodologies (Chen et al., J. Org. Chem., 58, p.1287; U.S. Pat. No. 6,020,174 to Chen et al.; Honig et al., Tetrahedron Letters, 46, p.3841, 1990; U.S. Pat. No. 5,773,629 to Yang et al.; and U.S. Pat. Nos. 5,811,292, 5,567,614 and 5,686,298 to Patel et al).

However, there remains a need to provide new and improved methods for the efficient and economical preparation of chiral compounds useful in taxane semi-synthesis. In particular, there remains a need for simple methods for producing chiral compounds useful as precursors for the C-13 side-chain esterification with a baccatin III backbone. The present invention is directed to meeting these needs.

SUMMARY OF THE INVENTION

It is an object of the present invention to provide a new and useful method for preparing chiral compounds useful in taxane semi-synthesis.

It is another object to provide methods for preparing optically pure derivatives of 3-phenylisoserine.

It is yet another object to provide for simple and efficient chiral chromatographic separation of optical isomers useful in the synthesis of taxanes such as paclitaxel and docetaxel.

A still further object is to provide chromatography media useful in chromatographically separating optical isomers of 3-phenylisoserine derivatives.

Yet another object is to synthesize an N-CBZ-(2R,3S)-3-phenylisoserine side chain derivative in optically pure form that is suitable for coupling with a suitable baccatin III derivative to provide paclitaxel after various synthetic transformations.

According to the present invention, a method is provided for processing a solution having a plurality of optical isomers, such as a racemic solution, thereby to obtain a (2R,3S) target isomer having a formula:

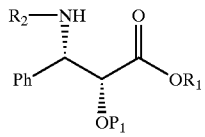

wherein $P_1$ is selected from H and a hydroxyl protecting group, $R_1$ is selected from H, an alkyl group, an olefinic group and an aromatic group, and $R_2$ is selected from H and $R_3CO$, where $R_3$ is selected from an alkyl group, an olefinic group, an aromatic group, an O-alkyl group, an O-olefinic group and an O-aromatic group. The method comprises the steps of passing the solution through a chromatographic stationary phase that has a greater affinity for either the target isomer or an optical isomer thereof, such that the target isomer passes through the stationary phase at a different rate than does the optical isomer thereof, and thereafter collecting a portion of the solution containing the target isomer.

The stationary phase may be loaded into a chromatography column having a first opening and a second opening, and the step of passing the solution through the stationary phase may be accomplished by injecting the solution into the first opening. The portion of the solution containing the target isomer may be collected from the second opening. Preferably, the solution contains the target isomer and the optical isomer thereof in a first ratio to one another, and the collected portion of the solution contains the target isomer and the optical isomer thereof in a second ratio to one another that is greater than the first ratio.

The stationary phase may include tetrahydrophenanthrene π systems, dinitrobenzamide π systems and amido-proton hydrogen bond donors, and preferably comprises S,S Whelk-O which may be covalently bonded to silica. The solution may include ethanol, isopropanol, hexane or the like, and preferably includes 20% isopropanol/80% hexane, and may contain about 0.025 g of the optical isomers per 1 mL isopropanol.

Various optical isomers are contemplated, including ones wherein $R_1$ is an alkyl group, $R_2$ is $R_3CO$ where $R_3$ is $PhCH_2O$, and wherein $P_1$ is hydrogen, and particularly a (2R,3S)-N-CBZ-3-phenylisoserine ethyl ester of the formula:

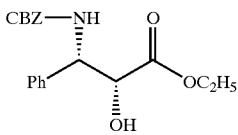

The present invention particularly contemplates a method of processing a racemic mixture of (±)-N-CBZ-3-phenylisoserine ethyl ester thereby to separate the (2R,3S) isomer from the enantiomer thereof, comprising chromatographing the racemic mixture by HPLC using a stationary phase comprising S,S Whelk-O and a mobile phase including ethanol, isopropanol or hexane. The HPLC peak for the (2R,3S) isomer is preferably resolved to the baseline from the HPLC peak for the enantiomer thereof.

Further, the invention may broadly include a method of processing optical isomers of the general formula:

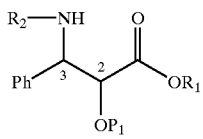

wherein $P_1$ is H or a hydroxyl protecting group, $R_1$ is selected from H, an alkyl group, an olefinic group and an aromatic group, and $R_2$ is selected from H and $R_3CO$, where $R_3$ is selected from an alkyl group, an olefinic group, an aromatic group, an O-alkyl group, an O-olefinic group and an O-aromatic group, thereby to separate the optical isomers from one another, comprising chromatographing the racemic mixture by HPLC using a stationary phase that has a different affinity for each of the optical isomers.

These and other objects of the present invention will become more readily appreciated and understood from a consideration of the following detailed description of the exemplary embodiments of the present invention when taken together with the accompanying drawings, in which:

DETAILED DESCRIPTION OF THE EXEMPLARY EMBODIMENTS OF THE INVENTION

The N-benzoyl-(2R,3S)-3-phenylisoserine side chain of the formula:

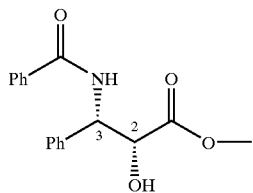

is crucial to the antitumor activity of paclitaxel. This side chain must be available in highly enantiomerically pure form for use in the partial synthesis of paclitaxel and its analogs. Analogs and derivatives of this side chain are also useful in forming other taxanes, such as docetaxel, which may be useful in the treatment of cancer.

The present invention provides a method for the chiral chromatographic resolution of racemic mixtures of enantiomers, such as (±)-N-CBZ-3-phenylisoserine ethyl ester, which may be employed as side chain precursors in the semi-synthesis of paclitaxel and its analogs that bear a C-13 side chain. The chiral resolution is achieved by preparative chiral column chromatography using columns packed with a stationary phase comprising an appropriate chromatographic media, such as S,S Whelk-O, 10μ FEC, which is operative to separate the enantiomers of the racemic mixture.

Figure 1:
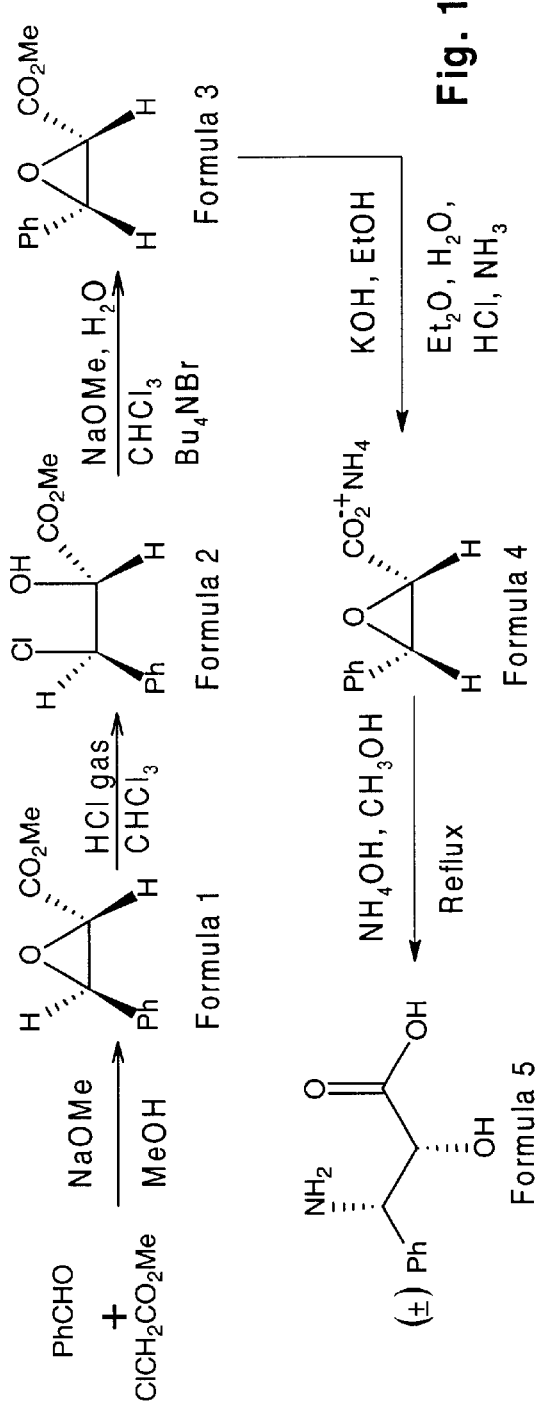
FIG. 1 is a diagram showing an exemplary chemical process according to the present invention for the preparation of racemic 3-phenylisoserine.
Figure 2:
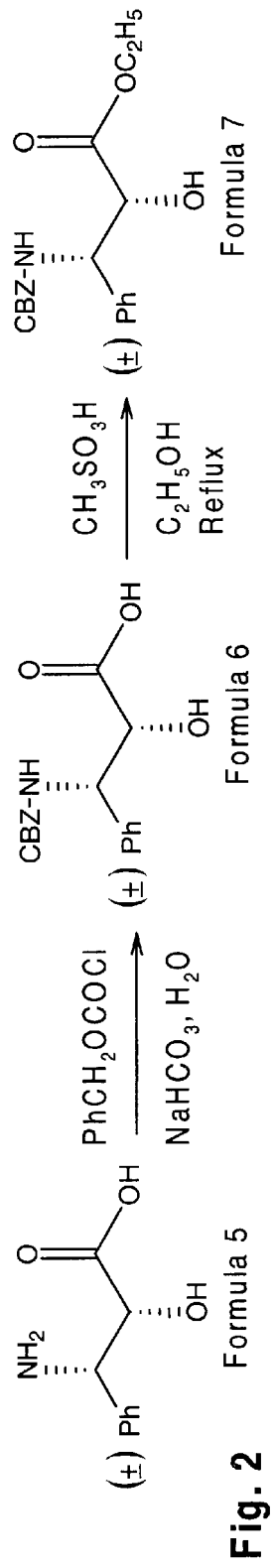
FIG. 2 is a diagram showing an exemplary chemical process for converting the racemic 3-phenylisoserine formed in FIG. 1 to a racemic 3-N-CBZ ethyl ester.

In the exemplary process, a racemic N-CBZ-3-phenylisoserine ethyl ester was synthesized according to the sequence shown with respect to FIGS. 1 and 2, and as discussed below. It should be appreciated, though, that the present invention contemplates the chiral chromatographic resolution of mixtures of other taxane side-chain precursor compounds, such as compounds having a 3-amino group, compounds utilizing 3-N-protecting groups other than CBZ, compounds protected at the 2-O-position, compounds having ester substituents other than an ethyl group, such as other alkyl groups and the like, or carboxylic acid derivatives of the side-chain ester compounds, as discussed more fully below.

A. Formation of Racemic Phenylisoserine

Racemic phenylisoserine of the formula:

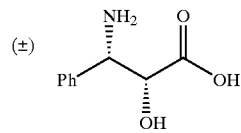

is first formed as described below. It should be appreciated that the starting materials and reagents used in the processes described herein are readily available from chemical suppliers, as would be understood by the ordinarily skilled artisan. Further, as apparent from the description of the various chemical steps herein, it should be appreciated that certain chemical steps in the processes were repeated at various scales to accumulate quantities of intermediate product for use in subsequent steps, while other steps used less than the total quantity of intermediate product produced in a previous step. However, it should be understood that adjustments in the quantities of materials may be made without departing from the general inventive concept, and in particular the individual chemical steps described herein may be scaled to accommodate quantities of materials produced in previous steps.

First, a Darzen's condensation of benzaldehyde with methylchloroacetate in the presence of sodium methoxide in methanol provides the trans-methyl 3-phenylglycidate (Formula 1), as follows:

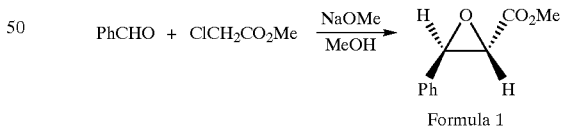

Formula 1

Here, benzaldehyde (1.76 Kg, 1.0 eq.) and methylchloroacetate (2.70 Kg, 1.5 eq.) were added to methanol (2.55 L/Kg benzaldehyde) in a dry 22 liter 3-necked round bottom flask equipped with a mechanical stirrer, condenser, thermometer, addition funnel, nitrogen purge, and ice/methanol bath. While stirring, the reaction mixture was cooled to between 0° C. and −10° C., and 1.5 eq. sodium methoxide (25% in methanol) was slowly titrated into the reaction mixture at the cooled temperature. The cooling bath was then removed and the flask was allowed to warm to room temperature naturally, via an overnight stir. The reaction was monitored by TLC and was deemed complete by the disappearance of starting materials. The reaction was worked-up by concentrating the mixture to approximately 20% of the starting volume under reduced pressure and at a temperature of ≦40° C. The concentrate was then quenched with purified water (10 L/Kg benzaldehyde) and extracted into ethyl ether (10 L/Kg benzaldehyde), and the extracts were dried over sodium sulfate (1.1 Kg/Kg benzaldehyde), treated with activated carbon, filtered, and concentrated to an oil, resulting in 81% yield of the trans isomer of Formula 1.

The trans epoxide of Formula 1 is next converted to the cis isomer (Formula 3) via oxirane opening with gaseous HCl in chloroform to form a chlorohydrin derivative (Formula 2) followed by ring closure with sodium methoxide in the presence of a phase transfer catalyst such as tetrabutylammonium bromide, in chloroform and water, as follows:

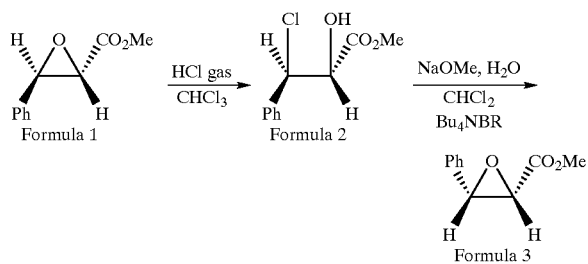

Here, a solvent, preferably chloroform (10 L/Kg trans epoxide), was added to a 3-necked, round bottom flask equipped with a mechanical stirrer, reflux condenser, nitrogen purge, gas dispersion tube and thermometer. Various solvents are contemplated, including chloroform, chloroform/hexane (10:90), toluene and benzene. While stirring, the methylphenyloxirane carboxylate of Formula 1 (2.4 Kg, 1.0 eq.) was added, and after dissolving, constant stirring continued and HCl gas was bubbled into the solution for at least 3 hours, after which the reaction mixture was allowed to stir overnight at a temperature of room temperature to 50° C. The reaction mixture was concentrated to an oil under reduced pressure at a temperature of ≦40° C. The oil was titrated with ethyl ether (1.25 L/kg trans epoxide) and cooled to 0° C. to force crystallization of the product of Formula 2 as a white solid. The solid was collected by filtration and washed with a hexane:ethyl ether (4:1) solution (6.25 L/kg trans epoxide), and the mother liquor was cooled to 0° C. for over 24 hours to recover further product. Further experiments indicate that use of a trans-ethyl 3-phenylglycidate significantly increased the yield of this step while maintaining the same level of purity.

Next, a solvent, preferably chloroform (8 L/Kg chlorohydrin), and purified water (2 L/Kg chlorohydrin) were added to a 3-necked round bottom flask equipped with a mechanical stirrer, reflux condenser, nitrogen purge, addition funnel and thermometer. The use of other solvents, such as THF or methanol, is contemplated. With stirring, the chlorohydrin derivative of Formula 2 (0.81 Kg, 1.0 eq.) was added, along with a phase transfer catalyst, such as between 0.1 and 0.3 eq. tetrabutyl-N-bromide ($Bu_4NBr$). These reactants were allowed to dissolve, followed by the addition of 1.5 to 2.0 eq. sodium methoxide (25% in methanol) at room temperature over a 15 minute period. It should be appreciated that other bases, such as NaOH or Amberlite, may be used in this step, such as with THF solvent. It should additionally be noted that the use of a phase transfer catalyst may not be necessary when weaker bases are used having increased solubility. The reaction progress was monitored by TLC and was deemed complete after 30 minutes of stirring at room temperature. The product (Formula 3) was worked up by phase separation, and the organic phase was washed twice with purified water, followed by drying over sodium sulfate, filtration, and concentration to an oil. Notably, the cis product of Formula 3 was found to be unstable after isolation, even under nitrogen at ≦10° C., such that it is desirable to minimize reaction and work-up time related to this step.

The resulting cis-methyl 3-phenylglycidate (Formula 3) was converted to an ammonium salt by saponification with KOH in ethanol followed by reaction with ammonia gas in the presence of aqueous HCl, water and ether:

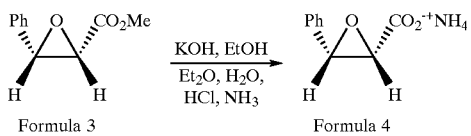

Here, a solvent, preferably ethanol (3 L/Kg of cis epoxide), was added to a 3-necked round bottom flask, equipped with a mechanical stirrer, reflux condenser, addition funnel, thermometer, ice-water bath and nitrogen purge. The use of other solvents, such as methanol, is contemplated. KOH (1.3 to 1.8 eq) was added with stirring, while maintaining the temperature between 0–5° C., followed by the slow addition of the oxirane derivative of Formula 3 in ethanol (0.66 Kg, 1.0 eq dissolved in 2 L/Kg of cis epoxide), over a time of 15–30 minutes. The temperature was maintained between 0–5° C. during the addition process and slowly raised to ambient temperatures by removing the ice-water bath.

The resulting reaction mixture was stirred for 3 hours and monitored by TLC for completion. The reaction mixture was cooled to 0–5° C. for complete precipitation of the intermediate product, (±)-potassium-(+)-3-phenyloxirane carboxylate as a white solid, which was filtered, washed with cold ethanol and dried in the vacuum oven at 35° C.

This potassium salt was added to a 3-necked round bottom flask, equipped with a mechanical stirrer, reflux condenser, addition funnel, thermometer, ice-water bath and nitrogen purge. Water (6 L/Kg of potassium salt) was added followed by cooling to ≦10° C. To this solution was added ether (5 L/Kg of potassium salt) and 1N HCl (5 L/Kg of potassium salt) while stirring vigorously at ≦10° C. Temperature was slowly raised to ambient temperatures by removing the ice-water bath and stirring continued for 30 min. The organic phase was separated and the aqueous phase was extracted with ether. The organic layers were combined and transferred to a 3-necked round bottom flask into which ammonia gas was bubbled at ambient temperatures for 30 minutes while continuously stirring. The reaction mixture was cooled to 0–5° C. and stirring continued for an additional 30 minutes. The resulting solid was filtered, washed with cold ether and dried to afford the ammonium salt of formula 4, in 69% yield.

The resulting (±)-ammonium-(+)-3-phenyloxirane carboxylate (Formula 4) was refluxed with ammonium hydroxide in methanol to provide the racemic phenylisoserine (Formula 5):

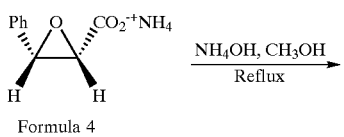

Formula 4

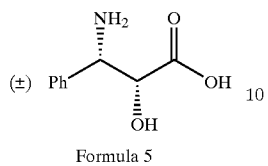

Formula 5

Here, the ammonium salt of Formula 4 (0.15 Kg, 1.0 eq.) was added to methanol (45 L/Kg ammonium salt), while stirring, in a 3-necked round bottom flask equipped with a mechanical stirrer, reflux condenser, thermometer, and heating mantle. Ammonium hydroxide (0.26 Kg/Kg ammonium salt) was added in 3 increments over a 16 hour period, in order to replenish lost ammonia. The reaction was allowed to reflux for 24 hours, and the mixture was concentrated to approximately 15% of starting volume, cooled to ≦10° C. to form a precipitate, filtered, and washed with ethyl ether to provide the racemic product of Formula 5 in greater than 90% yield.

It should be understood that the present invention contemplates the use of racemic phenylisoserine formed according to the method described herein or according to other methods, to the extent understood by the ordinarily skilled artisan. Further, it should be understood that the present invention contemplates the use of racemic phenylisoserine mixtures including one or more of the (2R,3R) and (2S,3S) diastereomers of the desired (2R,3S) isomer, in addition to one or more of the enantiomers thereof.

B. Conversion to N-protected Ester Precursor

The (±)-phenylisoserine (Formula 5) was next protected as its N-CBZ derivative using Schotten-Baumann conditions in the presence of benzylchloroformate, sodium bicarbonate and water to furnish (±)-N-CBZ-3-phenylisoserine (Formula 6), as follows:

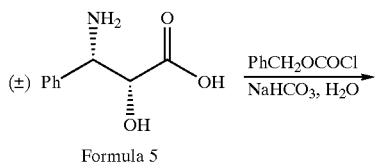

Formula 5

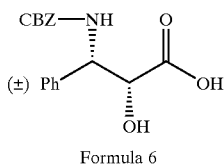

Formula 6

Here, the racemic 3-phenylisoserine of Formula 5 (0.08 Kg, 1.0 eq.) was added with agitation to a reaction flask containing a 10% aqueous solution of sodium bicarbonate (135 L/Kg phenylisoserine) under a nitrogen blanket, which was stirred until dissolved. The reaction mixture was then cooled to 0–5° C. and approximately 3 eq. benzyl chloroformate was added dropwise while maintaining the temperature of the mixture. The resulting solution was allowed to stir for 6 hours at ≦5° C. or until the disappearance of the racemic 3-phenylisoserine reactant was confirmed by TLC. Hydrochloric acid was added dropwise, with stirring, at room temperature to bring the mixture to a pH of ≦4. The mixture was extracted into ethyl acetate (200 L/Kg phenylisoserine), dried over sodium sulfate, filtered, and concentrated at ≦45° C. under reduced pressure to yield the crude product of Formula 6, which was purified by slurrying in 50:50 hexane/chloroform.

Although Formula 6 relates to the preferred embodiment of the present invention, it should be appreciated that other acylating agents may be used in place of benzyl chloroformate, to the extent understood by the ordinarily skilled artisan, to provide compounds having different chemical groups at the 3-N-position, such as compounds of the general formula:

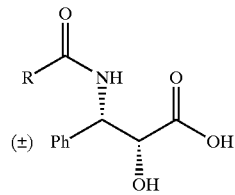

Formula 6a wherein R may be an alkyl group, olefinic group, aromatic group such as Ph, O-alkyl, O-olefinic, or O-aromatic group (such as PhCH$_2$O— in the case of the CBZ group). Alternatively, the present invention contemplates that the 3-amino group may remain unprotected during the chiral separation step discussed below.

The racemic N-CBZ-3-phenylisoserine of Formula 6 was then esterified by refluxing in ethanol with methane sulfonic acid to provide the (±)-N-CBZ-3-phenylisoserine ethyl ester (Formula 7) ready for chiral chromatographic separation:

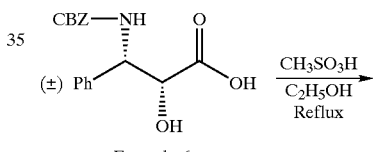

Formula 6

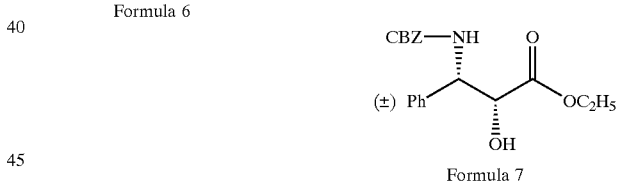

Formula 7

Here, Formula 6 (0.072 Kg, 1.0 eq.) was added to an excess of ethanol (230 L/Kg phenylisoserine) and 0.5 eq. methyl sulfonic acid in a 3-necked round bottom flask equipped with a mechanical stirrer, nitrogen purge, heating mantle, and thermometer. The reaction mixture was refluxed for 3 hours and was then concentrated at ≦45° C. under reduced pressure to yield an oil. The oil was dissolved in chloroform and the organics were washed once with 5% NaHCO$_3$, twice with purified water, dried over sodium sulfate, filtered and then concentrated to an oil, which solidified to an off-white residue while standing. The solid was slurried in hexane, filtered, and dried to provide purified racemic 3-N-CBZ-3-phenylisoserine ethyl ester of Formula 7 in greater than 90% yield.

Again, it should be appreciated that other esters of the acid of Formula 6 may be formed for use in the present invention, as known in the art. For example, other alkyl esters, such as methyl esters and the like, as well as aromatic and olefinic esters of the acid of Formula 6 are contemplated. Additionally, as indicated above, various other acyl groups may be utilized at the 3-N-position in place of the CBZ group, or alternatively the compound may remain free as the amine or amine salt for the chiral separation step discussed below. Furthermore, the present invention contemplates that the 2-hydroxyl may alternatively be protected, such as in the manner discussed below, prior to the chiral separation step.

Accordingly, it should be appreciated that the present invention contemplates the formation of various compounds for use in the chiral separation of the present invention, such as compounds of the general formula:

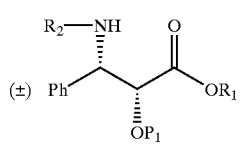

Formula 7a wherein $P_1$ is selected from H and a hydroxyl protecting group, $R_1$ is selected from H, an alkyl group, an olefinic group and an aromatic group, and $R_2$ is selected from H and $R_3CO$, where $R_3$ is selected from an alkyl group, an olefinic group, an aromatic group, an O-alkyl group, an O-olefinic group and an O-aromatic group. Table A below demonstrates, without limitation, various compounds of general Formula 7a contemplated by the present invention.

TABLE A

| Compound | $P_1$ | $R_1$ | $R_2$ | $R_3$ |
|---|---|---|---|---|
| 1 | H | H | H | — |
| 2 | H | H | $R_3CO$ | alkyl |
| 3 | H | H | $R_3CO$ | olefinic |
| 4 | H | H | $R_3CO$ | aromatic |
| 5 | H | H | $R_3CO$ | Ph |
| 6 | H | H | $R_3CO$ | O-alkyl |
| 7 | H | H | $R_3CO$ | O-olefinic |
| 8 | H | H | $R_3CO$ | O-aromatic |
| 9 | H | H | $R_3CO$ | O-CH$_2$Ph |
| 10 | H | alkyl | H | — |
| 11 | H | alkyl | $R_3CO$ | alkyl |
| 12 | H | alkyl | $R_3CO$ | olefinic |
| 13 | H | alkyl | $R_3CO$ | aromatic |
| 14 | H | alkyl | $R_3CO$ | Ph |
| 15 | H | alkyl | $R_3CO$ | O-alkyl |
| 16 | H | alkyl | $R_3CO$ | O-olefinic |
| 17 | H | alkyl | $R_3CO$ | O-aromatic |
| 18 | H | alkyl | $R_3CO$ | O-CH$_2$Ph |
| 19 | H | ethyl | H | — |
| 20 | H | ethyl | $R_3CO$ | alkyl |
| 21 | H | ethyl | $R_3CO$ | olefinic |
| 22 | H | ethyl | $R_3CO$ | aromatic |
| 23 | H | ethyl | $R_3CO$ | Ph |
| 24 | H | ethyl | $R_3CO$ | O-alkyl |
| 25 | H | ethyl | $R_3CO$ | O-olefinic |
| 26 | H | ethyl | $R_3CO$ | O-aromatic |
| 27 | H | ethyl | $R_3CO$ | O-CH$_2$Ph |
| 28 | H | methyl | H | — |
| 29 | H | methyl | $R_3CO$ | alkyl |
| 30 | H | methyl | $R_3CO$ | olefinic |
| 31 | H | methyl | $R_3CO$ | aromatic |
| 32 | H | methyl | $R_3CO$ | Ph |
| 33 | H | methyl | $R_3CO$ | O-alkyl |
| 34 | H | methyl | $R_3CO$ | O-olefinic |
| 35 | H | methyl | $R_3CO$ | O-aromatic |
| 36 | H | methyl | $R_3CO$ | O-CH$_2$Ph |
| 37 | H | olefinic | H | — |
| 38 | H | olefinic | $R_3CO$ | alkyl |
| 39 | H | olefinic | $R_3CO$ | olefinic |
| 40 | H | olefinic | $R_3CO$ | aromatic |
| 41 | H | olefinic | $R_3CO$ | Ph |
| 42 | H | olefinic | $R_3CO$ | O-alkyl |
| 43 | H | olefinic | $R_3CO$ | O-olefinic |
| 44 | H | olefinic | $R_3CO$ | O-aromatic |
| 45 | H | olefinic | $R_3CO$ | O-CH$_2$Ph |
| 46 | H | aromatic | H | — |
| 47 | H | aromatic | $R_3CO$ | alkyl |
| 48 | H | aromatic | $R_3CO$ | olefinic |
| 49 | H | aromatic | $R_3CO$ | aromatic |
| 50 | H | aromatic | $R_3CO$ | Ph |
| 51 | H | aromatic | $R_3CO$ | O-alkyl |
| 52 | H | aromatic | $R_3CO$ | O-olefinic |
| 53 | H | aromatic | $R_3CO$ | O-aromatic |
| 54 | H | aromatic | $R_3CO$ | O-CH$_2$Ph |
| 55 | hydroxyl protecting group | H | H | — |
| 56 | hydroxyl protecting group | H | $R_3CO$ | alkyl |
| 57 | hydroxyl protecting group | H | $R_3CO$ | olefinic |
| 58 | hydroxyl protecting group | H | $R_3CO$ | aromatic |
| 59 | hydroxyl protecting group | H | $R_3CO$ | Ph |
| 60 | hydroxyl protecting group | H | $R_3CO$ | O-alkyl |
| 61 | hydroxyl protecting group | H | $R_3CO$ | O-olefinic |
| 62 | hydroxyl protecting group | H | $R_3CO$ | O-aromatic |
| 63 | hydroxyl protecting group | H | $R_3CO$ | O-CH$_2$Ph |
| 64 | hydroxyl protecting group | alkyl | H | — |
| 65 | hydroxyl protecting group | alkyl | $R_3CO$ | alkyl |
| 66 | hydroxyl protecting group | alkyl | $R_3CO$ | olefinic |
| 67 | hydroxyl protecting group | alkyl | $R_3CO$ | aromatic |
| 68 | hydroxyl protecting group | alkyl | $R_3CO$ | Ph |
| 69 | hydroxyl protecting group | alkyl | $R_3CO$ | O-alkyl |
| 70 | hydroxyl protecting group | alkyl | $R_3CO$ | O-olefinic |
| 71 | hydroxyl protecting group | alkyl | $R_3CO$ | O-aromatic |
| 72 | hydroxyl protecting group | alkyl | $R_3CO$ | O-CH$_2$Ph |
| 73 | hydroxyl protecting group | ethyl | H | — |
| 74 | hydroxyl protecting group | ethyl | $R_3CO$ | alkyl |
| 75 | hydroxyl protecting group | ethyl | $R_3CO$ | olefinic |
| 76 | hydroxyl protecting group | ethyl | $R_3CO$ | aromatic |
| 77 | hydroxyl protecting group | ethyl | $R_3CO$ | Ph |
| 78 | hydroxyl protecting group | ethyl | $R_3CO$ | O-alkyl |
| 79 | hydroxyl protecting group | ethyl | $R_3CO$ | O-olefinic |
| 80 | hydroxyl protecting group | ethyl | $R_3CO$ | O-aromatic |
| 81 | hydroxyl protecting group | ethyl | $R_3CO$ | O-CH$_2$Ph |
| 82 | hydroxyl protecting group | methyl | H | — |
| 83 | hydroxyl protecting group | methyl | $R_3CO$ | alkyl |
| 84 | hydroxyl protecting group | methyl | $R_3CO$ | olefinic |
| 85 | hydroxyl protecting group | methyl | $R_3CO$ | aromatic |
| 86 | hydroxyl protecting group | methyl | $R_3CO$ | Ph |
| 87 | hydroxyl protecting group | methyl | $R_3CO$ | O-alkyl |

TABLE A-continued

| Compound | P₁ | R₁ | R₂ | R₃ |
|---|---|---|---|---|
| 88 | hydroxyl protecting group | methyl | R₃CO | O-olefinic |
| 89 | hydroxyl protecting group | methyl | R₃CO | O-aromatic |
| 90 | hydroxyl protecting group | methyl | R₃CO | O-CH₂Ph |
| 91 | hydroxyl protecting group | olefinic | H | — |
| 92 | hydroxyl protecting group | olefinic | R₃CO | alkyl |
| 93 | hydroxyl protecting group | olefinic | R₃CO | olefinic |
| 94 | hydroxyl protecting group | olefinic | R₃CO | aromatic |
| 95 | hydroxyl protecting group | olefinic | R₃CO | Ph |
| 96 | hydroxyl protecting group | olefinic | R₃CO | O-alkyl |
| 97 | hydroxyl protecting group | olefinic | R₃CO | O-olefinic |
| 98 | hydroxyl protecting group | olefinic | R₃CO | O-aromatic |
| 99 | hydroxyl protecting group | olefinic | R₃CO | O-CH₂Ph |
| 100 | hydroxyl protecting group | aromatic | H | — |
| 101 | hydroxyl protecting group | aromatic | R₃CO | alkyl |
| 102 | hydroxyl protecting group | aromatic | R₃CO | olefinic |
| 103 | hydroxyl protecting group | aromatic | R₃CO | aromatic |
| 104 | hydroxyl protecting group | aromatic | R₃CO | Ph |
| 105 | hydroxyl protecting group | aromatic | R₃CO | O-alkyl |
| 106 | hydroxyl protecting group | aromatic | R₃CO | O-olefinic |
| 107 | hydroxyl protecting group | aromatic | R₃CO | O-aromatic |
| 108 | hydroxyl protecting group | aromatic | R₃CO | O-CH₂Ph |

It should be appreciated that various hydroxyl protecting groups contemplated for $P_1$ in Table A above include, without limitation, benzyloxymethyl (BOM), benzyl, substituted benzyl, benzoyl, and the like.

Chiral Resolution of the Ester Precursor

Figure 3:
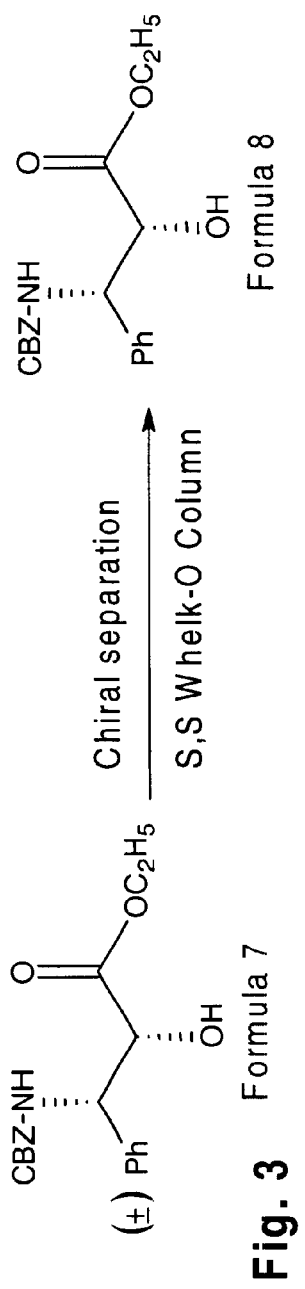
FIG. 3 is a diagram showing an exemplary chiral chromatographic separation to provide a chiral 3-N-CBZ-(2R, 3S)-ethyl ester from the racemic ethyl ester formed in FIG. 2.

As shown with reference to FIG. 3 and as discussed below, the racemic (±)-N-CBZ-3-phenylisoserine ethyl ester of Formula 7 (or a compound of the general formula 7a) is next purified by chiral chromatographic purification to separate the desired (2R,3S)-3-N-CBZ-3-phenylisoserine ethyl ester (Formula 8) from its enantiomer (and diastereomers if present), by using a chromatographic stationary phase that has a different affinity for the optical isomers, such that they pass through the stationary phase at different rates and are accordingly chromatographically separated, wholly or partially, from one another.

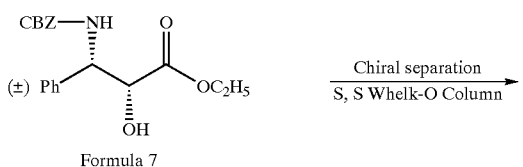

Formula 7

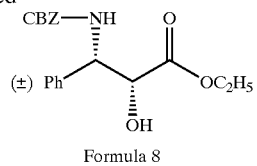

Formula 8

A number of columns and conditions were first evaluated using a racemic mixture of an N-benzoyl ethyl ester of the formula:

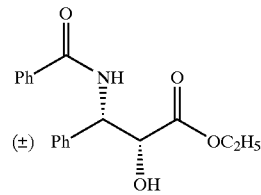

The results of this evaluation are shown in Table 1, below:

TABLE 1

| Column | Mobile Phase | K' of first eluted | α | Baseline Resolved? |
|---|---|---|---|---|
| S, S Whelk-O, 10μ FEC | 50% MTBE/ 48% Hexane/ 2% EtOH | 1.9 | 1.86 | Yes |
| S, S Whelk-O, 10μ FEC | 30% EtOH/ 70% Hexane | 0.786 | 1.32 | No |
| S, S Whelk-O, 10μ FEC | 20% EtOH/ 80% Hexane | 2.4 | 1.25 | No |
| S,S Whelk-O, 10μ FEC | 10% EtOH/ 90% Hexane | 3.8 | 1.35 | Barely |
| S,S Whelk-O, 10μ FEC | 30% n-BuOH/ 70% Hexane | 0.974 | 1.4 | No |
| Naproxen | various | — | — | n.s. |
| Napthyl Leucine | various | — | — | n.s. |
| Chiralcel OD | IPA/Hexane, EtOH/Hexane | — | — | n.s. |
| ChiralPak AD | 10% IPA/ 90% Hexane | 5.0 | 1.6 | Barely |

IPA: isopropanol
EtOH: ethanol
BuOH: butanol
MTBE: methyl t-butyl ether
n.s.: no separation
K': relative retention time of the compound
α: selectivity of the column
Baseline resolved: complete separation of the enantiomers to the HPLC baseline Based on these results, a number of conditions, including various mobile phases, were then evaluated to separate enantiomers of N-CBZ phenylisoserine ethyl ester of Formula 7, as shown in Table 2, below:

TABLE 2

| Column | Mobile Phase | K' of first eluted | α | Baseline Resolved? |
|---|---|---|---|---|
| S, S Whelk-O, 10μ FEC | 20% EtOH/ 80% Hexane | 2.13 | 1.45 | Yes |
| S, S Whelk-O, 10μ FEC | 7.5% IPA/ 7.5% EtOH/ 85% Hexane | 3.253 | 1.54 | Yes |
| S, S Whelk-O, 10μ FEC | 10% IPA/ 10% EtOH/ 80% Hexane | 2.549 | 1.54 | Yes |

TABLE 2-continued

| Column | Mobile Phase | K' of first eluted | α | Baseline Resolved? |
|---|---|---|---|---|
| S, S Whelk-O, 10μ FEC | 5% IPA/ 5% EtOH/ 90% Hexane | 4.603 | 1.56 | Yes |
| S, S Whelk-O, 10μ FEC | 20% IPA/ 80% Hexane | 2.69 | 1.63 | Yes |
| S, S Whelk-O, 10μ FEC | 50% MTBE/ 50% Hexane | 2.28 | 1.64 | Yes |
| S, S Whelk-O, 10μ FEC | 50% MTBE/ 48% Hexane/ 2% EtOH | 1.2 | 1.64 | Yes |

IPA: isopropanol
EtOH: ethanol
MTBE: methyl t-butyl ether
K' : relative retention time of the compound
α: selectivity of the column
Baseline resolved: complete separation of the enantiomers to the HPLC baseline Where a positive indication is given in the final column for "Baseline Resolved?", the chromatogram generally shows two distinct peaks, each rising from the approximate baseline and respectively corresponding to the two enantiomers, indicating virtually complete separation thereof. Where the final column indicates the baseline is "barely" resolved, the chromatogram generally shows two distinct peaks for which some overlap is observed above the baseline, suggesting partial but incomplete separation of the enantiomers. Where "n.s." is indicated in the final column, the chromatogram generally shows a single peak, suggesting little or no separation of the enantiomers. It should be noted that, under certain mixtures of alcohol/hexane mobile phases, two additional peaks appear on the chromatogram, which are believed to be the diastereomers. It should further be appreciated that additional minor peaks may be observed on the chromatogram, as generally understood in the art.

Interestingly, a racemic mixture of the benzoyl acid of the formula:

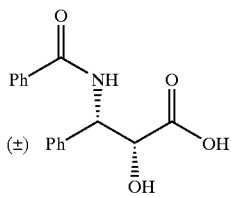

was not separated under any of the conditions attempted, such as those set forth in Tables 1 and 2.

The best conditions achieved for the separation of the ethyl ester enantiomers of Formula 7 employed a stationary phase comprising S,S Whelk-O bonded to 10μ Kromasil silica. This S,S Whelk-O stationary phase may be obtained from Regis Technologies, Inc., located in Morton Grove, Ill. In particular, various column lengths of the S,S Whelk-O covalently bonded to spherical silica, irregular silica, or spherical Kromasil silica, in various sizes such as 10μ and 5μ, are available from Regis Technologies. One version of this S,S Whelk-O stationary phase, identified by Regis Technologies as S,S Whelk-O 1, has a formula as follows:

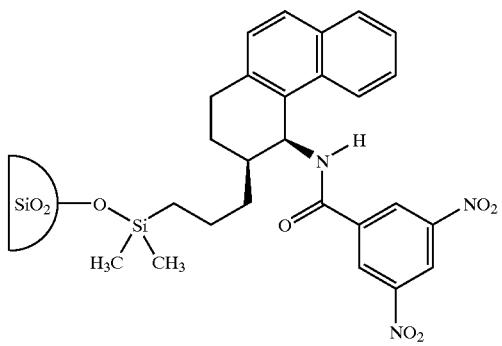

A variation of the S,S Whelk-O stationary phase, identified by Regis Technologies as S,S Whelk-O 2, has a covalent trifunctional linkage to the silica support. The present invention contemplates the use of either of these stationary phases, as well as other stationary phases/chromatographic media as discussed herein.

In the preferred process, the racemic CBZ-phenylisoserine ethyl ester was resolved into its respective enantiomers using a ProChrom HPLC system with an 8 cm diameter column containing 800 g of stationary phase, comprising fully endcapped S,S Whelk-O covalently bonded to 10/100 Kromasil silica. Whelk-O's key binding sites that affect the chromatographic separation are tetrahydrophenanthrene π systems and dinitrobenzamide π systems, in addition to amido-proton hydrogen bond donors. The mobile phase was 20% isopropanol/80% hexane; the flow rate was 300 mL per minute and detector wavelength was 220 nm. A solution of 0.025 g of racemate per 1 mL of isopropanol was prepared and successive 60 mL aliquots (equivalent to 1.5 g of the racemic material) were injected. The desired enantiomer elutes first and was collected separately. Solvent was removed under reduced pressures to obtain the optically pure (2R,3S)-N-CBZ-3-phenylisoserine ethyl ester product as white powder at 85% recovery.

It should be appreciated that other types of chromatographic media may be employed in the present invention, where such chromatographic media is operative to separate the enantiomers of racemic phenylisoserine ethyl ester and/or other compounds contemplated herein by chiral chromatographic resolution. For example, chromatographic media having as key binding sites one or more tetrahydrophenanthrene π systems, dinitrobenzamide π systems, or amido-proton hydrogen bond donors, or other similar binding sites, may be substituted for S,S Whelk-O in the stationary phase of the present invention. Additionally, it should be appreciated that the silica substrate may be substituted with other appropriate chromatographic substrates, to the extent known in the art.

It should further be understood that while it is preferred that the enantiomers are completely separated, such that chromatographic peaks corresponding thereto are resolved to the HPLC baseline, the present invention appreciates that less efficient separations may occur wherein some overlap of the HPLC peaks is observed.

D. Use of the Ester Precursor in Taxane Synthesis

Figure 4:
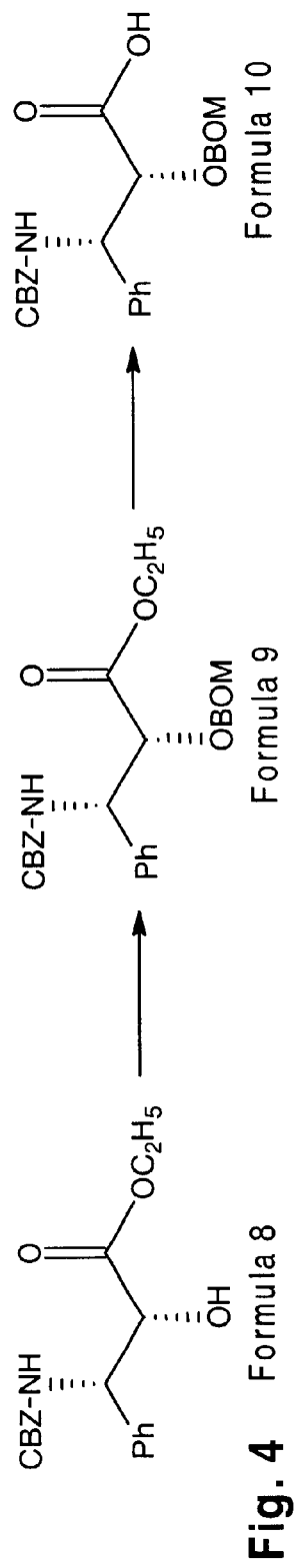
FIG. 4 is a diagram showing an exemplary chemical process for the protection and saponification of the chiral ethyl ester formed in FIG. 3.

After chiral chromatographic purification, the resulting optically pure, (2R,3S)-3-N-CBZ-3-phenylisoserine ethyl ester may be used in the production of desired taxanes, such as by various methods known in the art. For example, as shown with reference to FIG. 4 and as discussed below, Formula 8 may now be protected at the 2-O-position with a suitable protecting group, such as BOM, benzyl, substituted benzyl, benzoyl and the like, and may thereafter be saponified to the corresponding carboxylic acid thereby to provide a side chain precursor suitable for coupling with a baccatin III derivative to form desired taxanes, such as paclitaxel, docetaxel, or their analogs. Exemplary preparations of taxanes using a (2R,3S)-3-N-CBZ-3-phenylisoserine ethyl ester precursor are taught, for example, in U.S. Pat. Nos. 5,675,025; 5,684,175; 5,688,977; 5,750,737; 5,770,745; 5,939,566; 5,948,919; 6,048,990; 6,066,749; 6,072,060; 6,107,497; 6,136,999; and 6,143,902, the teachings of which are incorporated herein by reference.

For example, as taught in U.S. Pat. No. 5,750,737 to Sisti et al., the (2R,3S)-3-N-CBZ-3-phenylisoserine ethyl ester may be protected at the 2-hydroxy position with a benzyloxymethyl (BOM) group as follows:

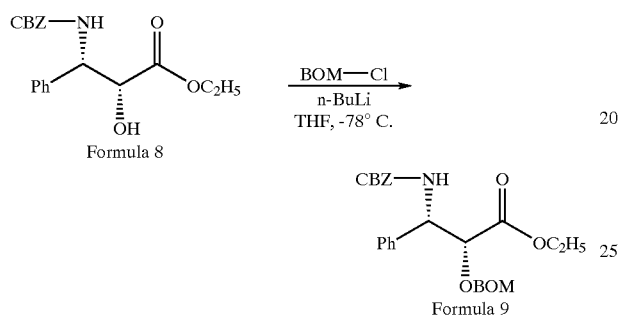

Here, the ethyl ester of Formula 8 is dissolved in anhydrous THF under a nitrogen atmosphere and cooled to a reduced temperature such as −40° C. or −78° C., for example, in a dry ice/acetone bath followed by the dropwise addition of an alkyllithium agent such as n-butyl lithium, although it is desirable that the alkyllithium agent be a straight chain alkyl. In any event, the reaction is best done at a temperature no greater than 0° C. The resulting mixture is stirred for about ten minutes. Benzyloxymethyl chloride (BOM-Cl) is then added dropwise over an interval of about five minutes, and the mixture stirred for approximately two to five hours at the reduced temperature. Thereafter, the solution is warmed to 0° C. and quenched with water to eliminate excess n-butyl lithium. The resulting mixture is concentrated under vacuum to residue, and this residue is thereafter taken up in ethyl acetate and washed with water and brine to remove unwanted salts. The organic layer may then be dried and concentrated under vacuum and the residue recrystallized from ethyl acetate:hexane or chromatographed with ethyl acetate:hexane to give the ethyl ester of Formula 9.

Formula 9 may then be saponified to its corresponding acid as follows:

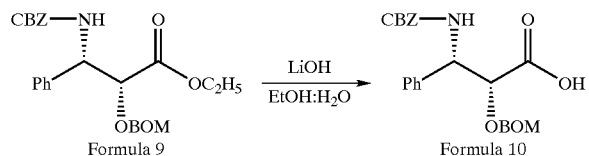

Here, Formula 9 is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1N hydrochloric acid) and extracted with ethyl acetate. The resulting organic layer is separated, dried and concentrated under vacuum. The residue acid is then isolated for use without further purification. This produces the acid of Formula 10.

Figure 5:
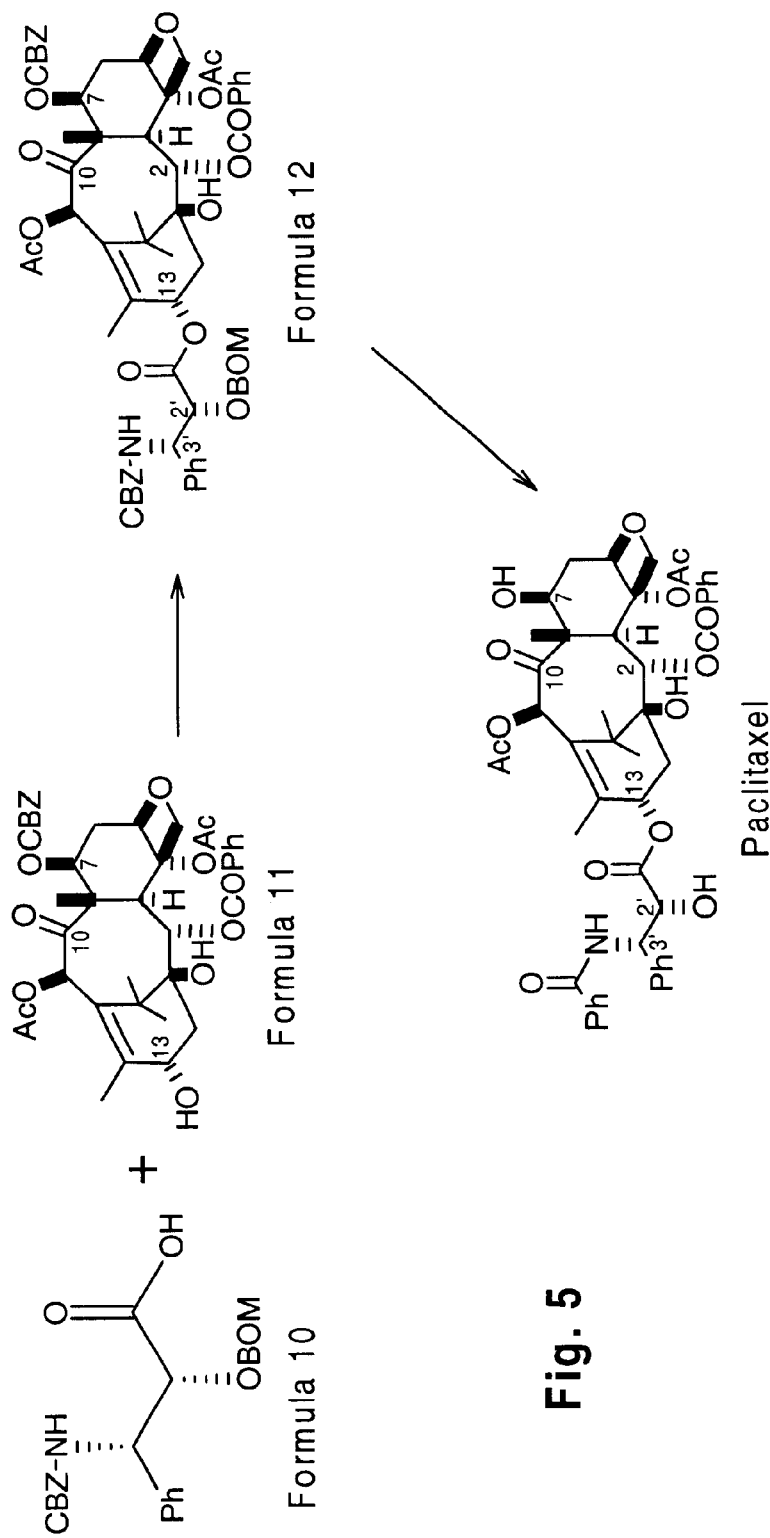
FIG. 5 is a diagram showing a generalized semi-synthesis of paclitaxel using the chiral 3-N-CBZ-2-O-BOM-(2R,3S)-3-phenylisoserine compound formed in FIG. 4.

As shown with reference to FIG. 5 and as discussed below, Formula 10 may then be coupled to a suitable taxane backbone, such as a protected baccatin III or 10-deacetylbaccatin III backbone, as known in the art, and the coupled product may thereafter be converted to paclitaxel or other taxanes. For example, as taught in U.S. Pat. No. 5,750,737, Formula 10 may be esterified with 7-CBZ baccatin III as follows:

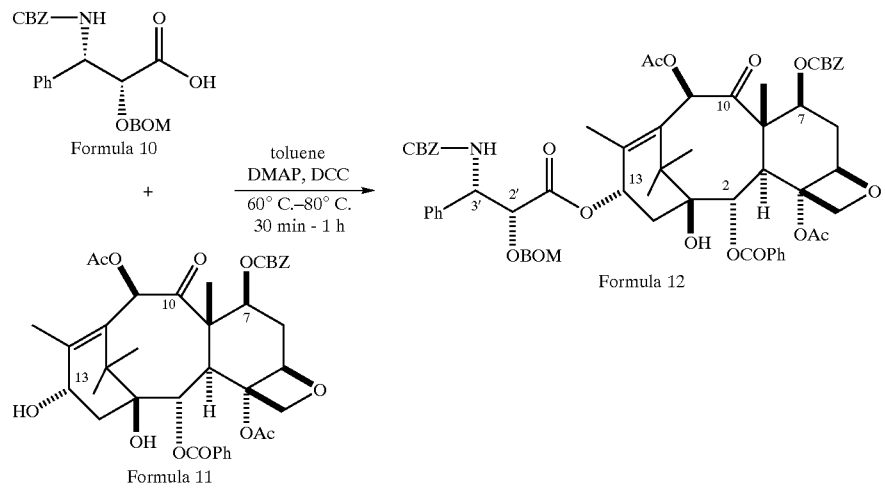

Here, Formula 11 (1 equivalent) and the acid side chain of Formula 10 (6 equivalents) are dissolved in toluene. To this mixture, 0.5 equivalents of dimethylamino pyridine (DMAP) and preferably 6 equivalents of dicyclohexylcarbodiimide (DCC) are added, and the resulting mixture heated at 70° C. for thirty (30) minutes to one (1) hour, although the range of temperature could be 60° C. to 80° C. Other dialkyl carbodiimides may be substituted for the DCC, with one example being diisopropylcarbodiimide. Next, the solution is cooled to room temperature and an equal volume of ethyl acetate or diethyl ether is added to the solution. The resulting mixture is then cooled to 0° C. and held at this temperature for twenty-four (24) hours. After this time it is filtered, and the residue is rinsed with either diethyl ether or ethyl acetate. The combined organics are then washed with hydrochloric acid (5%), water, and finally brine. The organic phase is separated, dried and concentrated under vacuum. The resulting residue is then dissolved in ethyl acetate:hexane and eluted over a silica gel plug. The eluent is then concentrated under vacuum to result in the esterified compound of Formula 12.

As further taught in U.S. Pat. No. 5,750,737, the 3'-N-CBZ and 7-O-CBZ protecting groups may be removed by hydrogenation, the 3'-N-amino group may be acylated using benzoyl chloride as the acylating agent to add a benzoyl group at the 3'-N-position, and the 2'-O-BOM protecting group may be removed by further hydrogenation, thereby to produce paclitaxel:

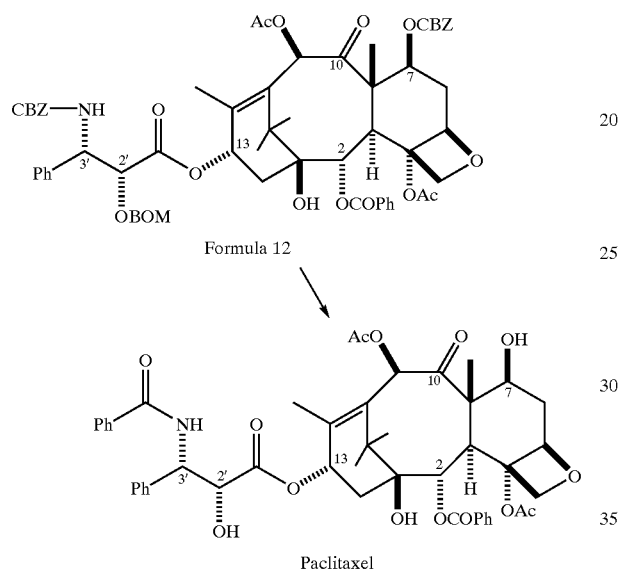

Formula 12

Paclitaxel

Here, the coupled product of Formula 12 is dissolved in isopropanol to which Pearlman's catalyst is added. The resulting mixture is hydrogenated at 40 psi for twenty-four hours, although alternatively, the mixture can be stirred under one atmosphere of hydrogen for 24 hours. Thereafter, the mixture is filtered through diatomaceous earth and reduced under vacuum to residue. Preferably, the residue is taken up in toluene and anhydrous potassium carbonate added. Alternatively, the residue may be taken up in ethyl acetate or toluene and a tertiary amine base, such as triethylamine, is added. In either case, benzoyl chloride is then added dropwise, and the mixture stirred for two hours. The resulting mixture is then washed with water and finally brine. The resulting organic phase is then separated, dried, and concentrated under vacuum to yield C2'-OBOM paclitaxel. The BOM group is removed by dissolving the C2'-OBOM paclitaxel in isopropanol to which Pearlman's catalyst is added. This mixture is hydrogenated for 24 hours under 40 psi hydrogen to yield paclitaxel.

Additional processes for the semi-synthesis of taxanes such as paclitaxel, docetaxel and the like using various suitable side chain precursors and baccatin III backbones are described, for example, in U.S. Pat. Nos. 5,675,025; 5,684,175; 5,688,977; 5,939,566; 5,948,919; 5,973,170; 6,048,990; 6,066,749; 6,072,060; 6,107,497; 6,133,462; 6,136,999; and 6,143,902, and the teachings thereof are incorporated herein by reference. It should be appreciated that the present invention is particularly adapted to provide suitable (2R,3S) side chain precursors for use in such processes.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

We claim:

1. A method of processing a solution having a plurality of optical isomers, thereby to obtain a (2R,3S) target isomer having a formula:

$$\begin{array}{c} R_2-NH \quad O \\ Ph \quad OR_1 \\ OP_1 \end{array}$$

wherein $P_1$ is selected from H and a hydroxyl protecting group, $R_1$ is selected from H, an alkyl group, an olefinic group and an aromatic group, and $R_2$ is selected from H and $R_3CO$, where $R_3$ is selected from an alkyl group, an olefinic group, an aromatic group, an O-alkyl group, an O-olefinic group and an O-aromatic group, provided that $R^1$ is not H when $R^3$ is Ph and $P^1$ is H, comprising the steps of:

(a) passing the solution through a chromatographic stationary phase that has a greater affinity for one of the target isomer and an optical isomer thereof, such that the target isomer passes through said stationary phase at a different rate than does said optical isomer thereof, said stationary phase having a formula and (b) collecting a portion of the solution containing the target isomer.

2. A method according to claim 1 wherein said stationary phase is loaded into a chromatography column having a first opening and a second opening, and wherein the step of passing the solution through said stationary phase is accomplished by injecting the solution into said first opening, and wherein said portion of the solution containing the target isomer is collected from said second opening.

3. A method according to claim 1 wherein the solution contains the target isomer and said optical isomer thereof in a first ratio to one another, and wherein said portion of the solution contains the target isomer and said optical isomer thereof in a second ratio to one another that is greater than said first ratio.

4. A method according to claim 1 wherein the solution is a racemic solution of the target isomer and said optical isomer thereof.

5. A method according to claim 1 wherein the solution includes a diastereomer of the target isomer.

6. A method according to claim 1 wherein said stationary phase comprises a chromatographic media covalently bonded to silica.

7. A method according to claim 1 wherein the solution includes a solvent selected from ethanol, isopropanol and hexane.

8. A method according to claim 1 wherein the solution includes 20% isopropanol/80% hexane.

9. A method according to claim 8 wherein the solution contains about 0.025 g of said optical isomers per 1 mL isopropanol.

10. A method according to claim 1 wherein $R_1$ is an alkyl group.

11. A method according to claim 1 wherein $R_2$ is $R_3CO$ and wherein $R_3$ is $PhCH_2O$.

12. A method according to claim 1 wherein $P_1$ is H.

13. A method according to claim 1 wherein the target isomer is a (2R,3S) ethyl ester of the formula:

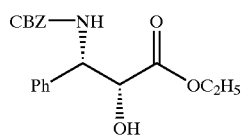

14. A method of separating a target isomer from an optical isomer thereof, wherein the target isomer has a formula:

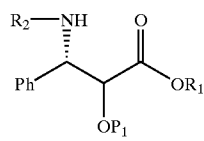

wherein $P_1$ is selected from H and a hydroxyl protecting group, $R_1$ is selected from H, an alkyl group, an olefinic group and an aromatic group, and $R_2$ is selected from H and $R_3CO$, where $R_3$ is selected from an alkyl group, an olefinic group, an aromatic group, an O-alkyl group, an O-olefinic group and an O-aromatic group, provided that $R^1$ is not H when $R^3$ is Ph and $P^1$ is H, the method comprising the steps of:
 (a) passing the solution from an upstream location to a downstream location through a chromatographic stationary phase that has a greater affinity for one of the target isomers and the optical isomer thereof, wherein said stationary phase is loaded into a single chromatography column and wherein said stationary phase comprises a chromatographic media that includes binding sites selected from tetrahydrophenanthrene π systems, dinitrobenzamide π systems, and amido-proton hydrogen bond donors; and
 (b) collecting the solution in a plurality of stages, each stage correlating to a portion of the solution collected over a respective interval of time thereby to form a respective collection solution, wherein the target isomer and the optical isomer thereof are in a first ratio to one another in a first collection solution and a second ratio to one another in a second collection solution, said first ratio being different than said second ratio.

15. A method of processing a racemic mixture of (±)-N-CBZ-3-phenylisoserine ethyl ester of the formula:

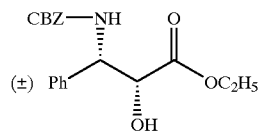

thereby to separate a (2R,3S) isomer from an enantiomer thereof, comprising chromatographing said racemic mixture by HPLC using a stationary phase comprising a substance having the general formula

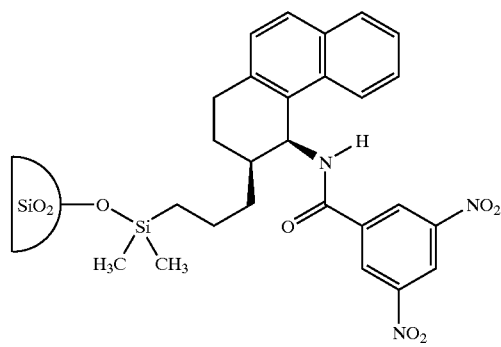

and a mobile phase including a solvent selected from ethanol, isopropanol and hexane.

16. A method according to claim 15 wherein said mobile phase is 20% isopropanol/80% hexane.

17. A method according to claim 15 wherein said mobile phase includes about 0.025 g of the (±)-N-CBZ-3-phenylisoserine ethyl ester per 1 mL of solvent.

18. A method according to claim 15 wherein an HPLC peak for the (2R,3S) isomer is resolved to a baseline from an HPLC peak for the enantiomer thereof.

19. A method of processing a mixture including optical isomers of the general formula:

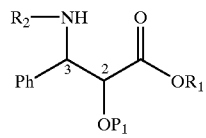

wherein $P_1$ is selected from H and a hydroxyl protecting group, $R_1$ is selected from H, an alkyl group, an olefinic group and an aromatic group, and $R_2$ is selected from H and $R_3CO$, where $R_3$ is selected from an alkyl group, an olefinic group, an aromatic group, an O-alkyl group, an O-olefinic group and an O-aromatic group, provided that $R^1$ is not H when $R^3$ is Ph and $P^1$ is H, thereby to separate the optical isomers from one another, comprising chromatographing the mixture by HPLC using a stationary phase that has a different affinity for each of the optical isomers, and wherein said stationary phase is loaded into a single chromatography column and has the general formula

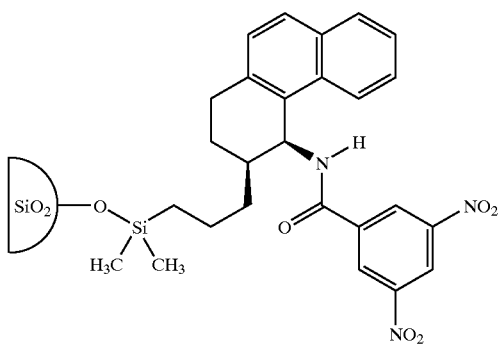

20. A method according to claim 19 wherein the mixture is a racemic mixture of enantiomers of the formula:

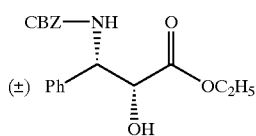

21. A method according to claim 19 including using a mobile phase including a solvent selected from ethanol, isopropanol and hexane.

22. A method according to claim 19 wherein $R_1$ is an alkyl group.

23. A method according to claim 19 wherein $R_2$ is $R_3CO$ and wherein $R_3$ is $PhCH_2O$.

24. A method according to claim 19 wherein $P_1$ is H.

25. A method of processing a mixture that includes a (2R,3S) isomer of the formula:

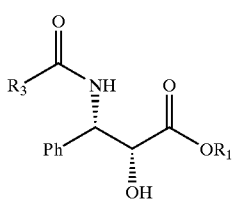

where $R_1$ is an alkyl group and $R_3$ is selected from an alkyl group, an olefinic group, an aromatic group, an O-alkyl group, an O-olefinic group and an O-aromatic group, and that includes a (2S,3R) enantiomer thereof of the formula:

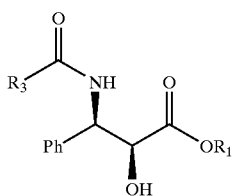

comprising chromatographing the mixture using a stationary phase that has a greater affinity for one of the (2R,3S) isomer and the (2S,3R) enantiomer thereof, wherein said stationary phase is loaded into a single chromatography column and has the general formula

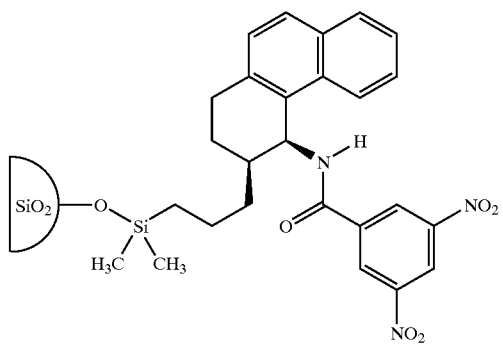

26. A method according to claim 25 wherein $R_1$ is an ethyl group.

27. A method according to claim 25 wherein $R_3$ is $PhCH_2O$.

28. A method according to claim 25 wherein $R_1$ is an ethyl group and wherein $R_3$ is $PhCH_2O$.

29. A method according to claim 25 wherein $R_1$ is an ethyl group, $R_3$ is $PhCH_2O$, and wherein said stationary phase comprises S,S Whelk-O.

30. A method of processing a solution having a plurality of optical isomers, thereby to obtain a (2R,3S) target isomer having a formula:

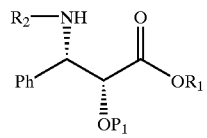

wherein $P_1$ is selected from H and a hydroxyl protecting group, $R_1$ is selected from H, an alkyl group, an olefinic group and an aromatic group, and $R_2$ is a carbamate N-protecting group, comprising the steps of:

(a) passing the solution through a chromatographic stationary phase that has a greater affinity for one of the target isomer and an optical isomer thereof, such that the target isomer passes through said stationary phase at a different rate than does said optical isomer thereof wherein said stationary phase is loaded into a single chromatographic column and wherein said stationary phase comprises a chromatographic media that includes binding sites selected from the group consisting of tetrahydrophenanthrene π systems, dinitrobenzamide π systems and amido-proton hydrogen bond donors; and (b) collecting a portion of the solution containing the target isomer.

31. A method according to claim 14 wherein said stationary phase has the formula

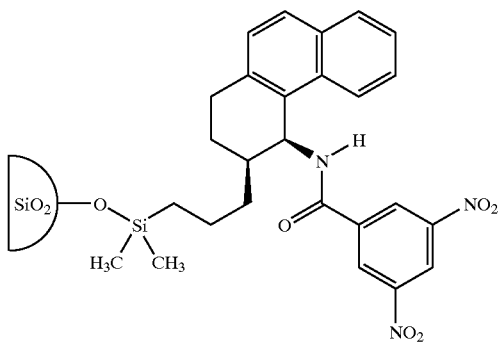

32. A method of processing a solution having a plurality of optical isomers, thereby to obtain a (2R,3S) target isomer having a formula:

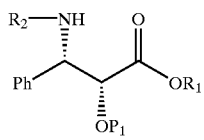

wherein $P_1$ is selected from H and a hydroxyl protecting group, $R_1$ is selected from H, an alkyl group, an olefinic group and an aromatic group, and $R_2$ is selected from H and $R_3CO$, where $R_3$ is selected from an alkyl group, an olefinic group, an aromatic group, an O-alkyl group, an O-olefinic group and an O-aromatic group, provided that $R^1$ is not H when $R^3$ is Ph and $P^1$ is H, comprising the steps of:
(a) passing the solution through a chromatographic stationary phase that has a greater affinity for one of the target isomers and an optical isomer thereof, such that the target isomer passes through said stationary phase at a different rate than does said optical isomer thereof, wherein said stationary phase is loaded into a single chromatography column and wherein said stationary phase comprises a chromatographic media that includes binding sites selected from the group consisting of tetrahydrophenanthrene π systems, dinitrobenzamide π systems and amido-proton hydrogen bond donors; and
(b) collecting a portion of the solution containing the target isomer.

33. A method according to claim 32 wherein the solution includes a solvent selected from ethanol, isopropanol and hexane.

34. A method according to claim 32 wherein the solution includes 20% isopropanol/80% hexane.

35. A method according to claim 34 wherein the solution contains about 0.025 g of said optical isomers per 1 mL isopropanol.

36. A method according to claim 32 wherein $R_1$ is an alkyl group.

37. A method according to claim 32 wherein $R_2$ is $R_3CO$ and wherein $R_3$ is $PhCH_2O$.

38. A method according to claim 32 wherein $P_1$ is H.

39. A method according to claim 32 wherein the target isomer is a (2R,3S) ethyl ester of the formula:

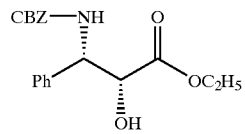

* * * * *